US008163091B2

(12) United States Patent
Frenzel et al.

(10) Patent No.: US 8,163,091 B2

(45) Date of Patent: Apr. 24, 2012

(54) EXTRACTION OF INGREDIENTS FROM BIOLOGICAL MATERIAL

(75) Inventors: Stefan Frenzel, Weinheim (DE); Thomas Michelberger, Grünstadt (DE); Günter Witte, Ramsen (DE)

(73) Assignee: Sudzucker Aktiengesellschaft Mannheim, Ochsenfurt (DE)

( * ) Notice: Subject to any disclaimer, the term of this patent is extended or adjusted under 35 U.S.C. 154(b) by 1341 days.

(21) Appl. No.: 10/539,781

(22) PCT Filed: Dec. 18, 2003

(86) PCT No.: PCT/EP03/14442

§ 371 (c)(1), (2), (4) Date: Sep. 20, 2005

(87) PCT Pub. No.: WO2004/055219

PCT Pub. Date: Jul. 1, 2004

(65) Prior Publication Data

US 2006/0106210 A1 May 18, 2006

(30) Foreign Application Priority Data

Dec. 18, 2002 (DE) .................................. 102 60 983

(51) Int. Cl.
*C07H 1/00* (2006.01)

(52) U.S. Cl. ................ 127/42; 127/43; 127/41; 127/44; 99/451; 536/124

(58) Field of Classification Search .................... 100/37; 127/53

See application file for complete search history.

(56) References Cited

U.S. PATENT DOCUMENTS

| | | | | |
|---|---|---|---|---|
| 3,477,873 | A | 11/1969 | Koelsh et al. | |
| 4,323,007 | A * | 4/1982 | Hunt et al. | 100/37 |
| 4,608,920 | A | 9/1986 | Scheglov et al. | |
| 4,787,303 | A | 11/1988 | Papchenko et al. | |
| 4,806,475 | A * | 2/1989 | Gould | 435/165 |
| 4,816,078 | A * | 3/1989 | Schiweck et al. | 127/36 |
| 4,831,127 | A * | 5/1989 | Weibel | 536/56 |
| 4,923,981 | A * | 5/1990 | Weibel et al. | 536/56 |
| 5,008,254 | A * | 4/1991 | Weibel | 514/57 |
| 6,387,186 | B1 * | 5/2002 | Reisig et al. | 127/55 |
| 6,656,287 | B2 * | 12/2003 | Sanders | 127/53 |

FOREIGN PATENT DOCUMENTS

| | | |
|---|---|---|
| CH | 661 411 A | 7/1987 |
| CH | 661411 | 7/1987 |
| DE | 2402947 | 1/1974 |
| DE | 24 02 947 | 7/1975 |
| DE | 3150314 | 12/1981 |
| DE | 3233282 | 9/1982 |
| DE | 31 50 314 | 7/1983 |
| DE | 32 33 282 A1 | 3/1984 |

(Continued)

OTHER PUBLICATIONS

"Processing of Sugar Beets With Pulsed-Electric Fields" by Christoph Schultheiss. IEEE Transactions on Plasma Science, vol. 30, No. 4, Aug. 2002.*

(Continued)

*Primary Examiner* — Melvin Mayes
*Assistant Examiner* — Colette Nguyen
(74) *Attorney, Agent, or Firm* — Ostrolenk Faber LLP

(57) ABSTRACT

The present invention relates to an improved method for isolating ingredients from biological material, in particular from sugar beet (*Beta vulgaris*).

26 Claims, 1 Drawing Sheet

FOREIGN PATENT DOCUMENTS

| | | | |
|---|---|---|---|
| DE | 10210554 | | 3/2002 |
| DE | 102 10 554 | | 12/2002 |
| EP | 0092466 | | 4/1983 |
| EP | 1257413 | | 11/2002 |
| FR | 2568820 | | 12/1984 |
| FR | 2 568 820 | | 2/1986 |
| FR | 2779741 | | 12/1999 |
| JP | S38-002187 | | 2/1963 |
| JP | S38-007063 | | 7/1963 |
| JP | S43-025094 | | 11/1964 |
| JP | S46-005779 | | 2/1971 |
| JP | 2-500948 | | 4/1990 |
| JP | 11-318500 | | 11/1999 |
| JP | 2000-109453 | | 4/2000 |
| JP | 2001-514268 | | 9/2001 |
| PL | 192311 | | 11/2001 |
| SU | 1521439 | | 11/1989 |
| WO | WO 99/10384 | | 4/1999 |
| WO | WO 99/64634 | | 12/1999 |
| WO | WO0162482 | * | 8/2001 |

OTHER PUBLICATIONS

Processing of Sugar Beets With Pulsed-Electric Field. IEEE Transactions on Plasma Sciences, vol. 30, No. 4, Aug. 2002). by Schultheiss.*

"High electric field pulse treatment: potential for sugar beet processing," M. N. Eshtiaghi et al., Journal of Food Engineering 52 (2002) 265-272.

"Beet juice extraction by pressing and pulsed electric fields," H. Bouzrara et al., Int. Sugar Jnl., 2000, vol. 102, No. 1216, 194-200.

"Cossette pretreatment and pressing," G. C. Jones, Int. Sugar Jnl., 1988, vol. 90, No. 1077, 157-167.

"Liming of sugar beet cossettes," A. E. Goodban et al., J. Amer. Sugar Beet Technol., 1965 (13) 566-572.

"Effects of lime on the chemistry of sugar beet tissue," W.M. Camirand, et al., J. Amer. Soc. Sugar Beet Technol., 1981 21 (2) 159-174.

"Pressing of cossettes after alcaline pretreatment," K.M. Bliesener, et al., Assembly Commission Internationale Technique de Sucrerie 19, 393-406 (1991).

"Wie kommt der Zucker aus der Rübe?" Presseinformation Forschungszentrum Karlsruhe 31/2001.

Joachim Hoffmann: "Wie kommt der Zucker aus der Rube" Online! Dec. 13, 2002, IDW , XP002276912 Gefunden im Internet: URL:http://home.arcor.de/ro/robertvandyk/ruebei.doc) das ganze Dokument.

International Search Report PCT/Ep03/14442 dated Apr. 14, 2004.

English translation of Ukraine Office Action corresponding to parallel Ukrainian Patent Application No. 2000021165.

English translation of relevant portions of "Method of Re-treatment of Vegetable Raw materials", the USSR Inventor's Certificate No. 1,521,439 published in the Bulletin No. 42, 1989.

English translation of relevant portions of "Method for Electric Plasmolysis of Ground Vegetable Raw Materials", the USSR Inventor's Certificate No. 212,147 published in the Bulletin No. 8, 1968.

English translation of Japanese Office Action corresponding to Japanese Patent Application No. 2004-560471.

C. Schultheiss et al., "Processing of Sugar Beets with Pulsed-Electric Fields", IEEE Transactions of Plasma Science, vol. 30, No. 4, Aug. 2002.

Office Action dated Jan. 5, 2010 in corresponding Polish Patent Application No. P-376320 (in Polish language).

Letter from Polish associate dated Jan. 28, 2010 forwarding the Polish Office Action dated Jan. 5, 2010 to German associate, including discussion of relevancy thereof.

New Zealand Examination Report dated Mar. 10, 2008.

* cited by examiner

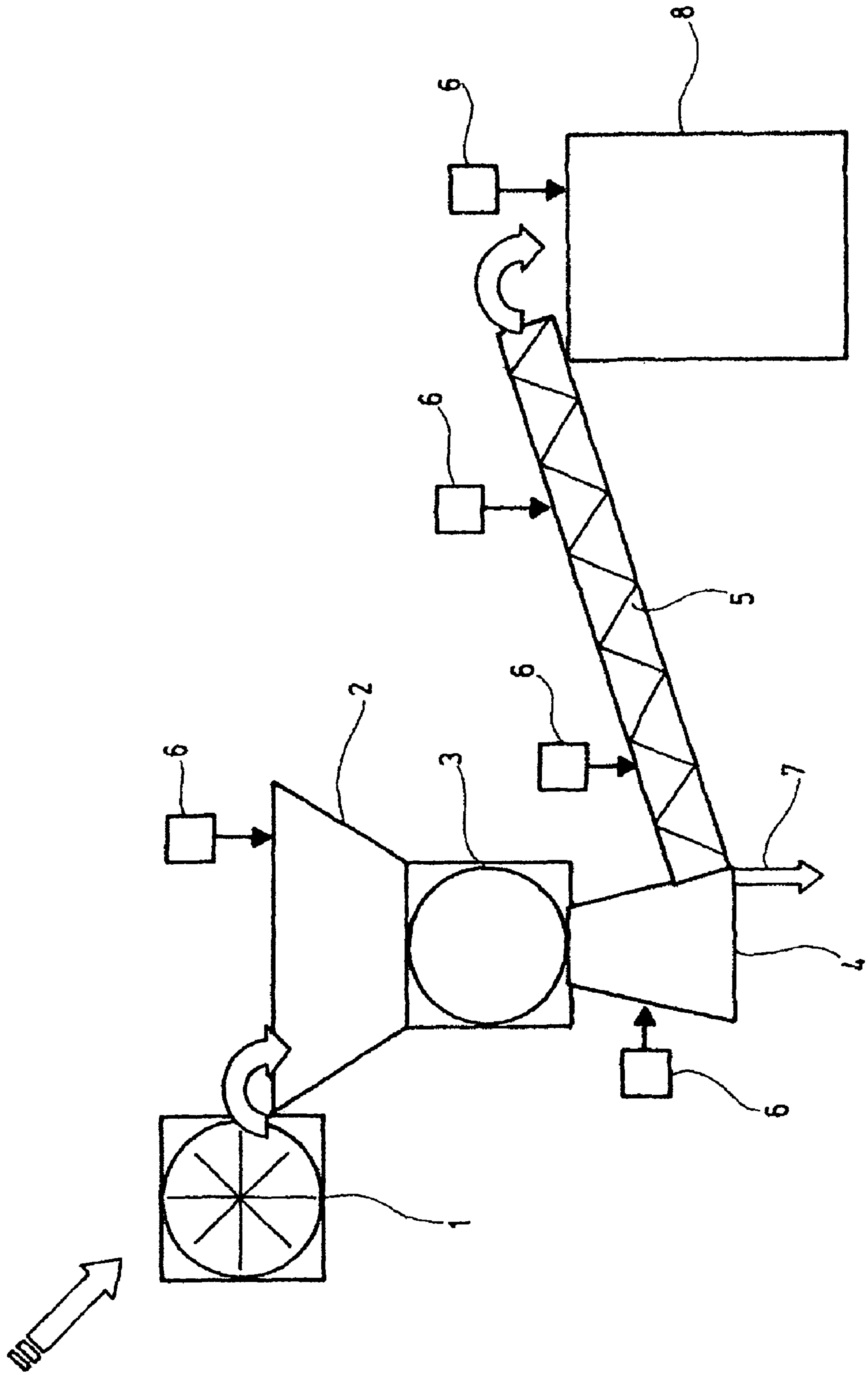
8
6
6
5
6
2
6
3
7
4
6
1

EXTRACTION OF INGREDIENTS FROM BIOLOGICAL MATERIAL

CROSS REFERENCE TO RELATED APPLICATIONS

The present application is a 35 U.S.C. §371 national phase conversion of PCT/EP2003/014442 filed 18 Dec. 2003, which claims priority of German Application No. 102 60 983.7 filed on 18 Dec. 2002.

The PCT International Application was published in the German language.

FIELD OF THE INVENTION

The present invention relates to a method for improving the isolation of ingredients from biological material, in particular from sugar beet (*Beta vulgaris* and/or sugar-beet chips.

BACKGROUND OF THE INVENTION

As is known, mechanical and/or thermal methods are used to isolate valuable ingredients from a large number of different biological materials, in particular raw plant materials such as agriculturally obtained fruit. In order to be able to separate off these ingredients from the biological material, the membranes of the cell material, in particular of the plant cell, have in every case to be opened. As a rule, this takes place by the action of mechanical forces such as chopping, grinding, rolling, etc. Other methods for disrupting the cell membranes of the biological material are thermal disruption, with the cell membranes being denatured by the influence of temperature, or a combination of thermal methods and mechanical methods. Following on from the disruption process, the soluble ingredients of the biological material are pressed out, extracted with solvent, usually water, or, in the case of insoluble substances, flushed out.

Such methods for isolating ingredients from biological material are particularly relevant for the sugar industry since, as is known, it is necessary, for the purpose of obtaining sugar (sucrose) in central Europe, to process sugar beet (*Beta vulgaris*) using these methods in order to obtain the sugar from the beet. In this connection, the washed beet are traditionally chipped in conventional cutting machines and the resulting chips are scalded, in a chip mash, with hot water at approximately 70 to 75° C. During this procedure, the beet cells are thermally denatured, i.e. the cell walls become disrupted and thereby permeable to sucrose molecules. In a subsequent extraction process, usually performed by means of countercurrent extraction, a sucrose-containing extract (raw juice) is obtained at temperatures of from approximately 68 to 70° C.

As is known, a substantial proportion of extraneous water (condensate) has to be added for the extraction to be effective. In order to optimize the extraction process and reduce the residual content of sugar in the extracted chips, approximately 105% to 110% raw juice, in relation to the quantity of chips, is usually withdrawn in the known methods. The withdrawal is calculated from the ratio of the quantity of extract to the quantity of beet employed. After that, a juice clarification of the extract can be carried out.

In addition to the substantial quantity of extraneous water which is required for the extraction, the processing of biological material for the purpose of isolating the ingredients is also a process which consumes a great deal of energy. In particular, the thermal disruption of the biological material at customary temperatures of more than 70° C. demands a high energy input. However, a substantial proportion of extraneous water also has to be heated to temperatures of more than 70° C. for the extraction step which follows and then evaporated once again at high energy cost in the subsequent course of the process. There is therefore a need, from the prior art, to disrupt biological material, in particular sugar beet or sugar beet cells, with a low consumption of energy and, by means of using a suitable downstream method, to reduce the quantity of water and energy which is required for isolating the ingredients from the biological material.

Another and important aspect is the extent to which the extracted biological material can be dewatered. For example, about 27 million tons of sugar beet are processed annually in the Federal Republic of Germany for the purpose of obtaining sugar. Following the aqueous countercurrent extraction of the comminuted beet, 15 million tons of extracted chips which have a water content of about 90% and which are used as cattle feed then accrue. In order to make the product stable and transportable, it has to be extensively dewatered. The dewatering firstly takes place mechanically, by means of pressing, and then by drying down to a residual water content of about 10%. In principle, a higher degree of pressing-out means a higher consumption of electrical energy, which consumption has to be set against the reduced consumption of fuel for the drying. Since the costs of the mechanical dewatering up to a dry matter content of what has previously been about 35% are markedly more advantageous than those for the drying, improving the pressing-out is a consistent aim of the sugar industry. The cost pressure in connection with the drying, and the environmental protection measures associated therewith, have led to the mechanical dewatering being steadily improved. The average dry matter content of pressed chips, as determined in 16 selected factories, rose from barely 20% in 1976 to on average approx. 32% in 1987. While about 44% of the water which has been carried through together with the extracted chips has still to be removed after the extracted chips have been pressed out to give a dry matter content of 20%, this proportion of water has already fallen to approx. 25% when pressing out has taken place to give 30% dry matter. This represents a substantial saving on energy which can amount to approx. 500 000 EUR per season (assumed oil price: 150 EUR/ton) in the case of a factory which processes 10 000 tons of beet per day. There is, therefore, an urgent need to further improve the ability of the biological material, in particular of the sugar beet chips, to be pressed out, that is to be dewatered, after the extraction.

SUMMARY OF THE INVENTION

The object of the present invention is to provide an improved method for isolating ingredients from biological material as well as a device for implementing the improved method, with the improved method being characterized, in particular, by a high degree of efficiency and economic viability which are concomitantly associated with a low consumption of resources such as energy and water.

According to the invention, the object is achieved by means of a method in which, for the purpose of isolating ingredients from biological material, the biological material is subjected to an electroporation in a first step a), the cell juice of the electroporated biological material is separated off in a second step b), the material obtained from step b) is subjected to an extraction in a third step c), and the ingredients are isolated from the cell juice obtained in step b) and from the extract obtained in step c) in a fourth step d).

The electroporation which is carried out in accordance with the invention particularly advantageously opens the cells of the biological material, in particular the beet cells, using high-voltage impulses. These cells do not need, therefore, to be thermally opened for a downstream extraction. The pretreatment of the biological material which is subsequently carried out enables the cell juice, in particular a large or substantial part of the cell juice, to be separated off in advance, advantageously reducing the quantity of the ingredients of the biological material which are to be extracted in the extraction step which is located downstream in accordance with the invention. This particularly advantageously results in a noticeable reduction in the requisite quantity of extraneous water which has to be used for extracting the ingredients which remain in the biological material after the above-mentioned removal of the cell juice. This also leads to a noticeable reduction in the withdrawal, that is the ratio of the quantity of extract to the quantity of biological material employed.

In connection with the present invention, "biological material" is understood as meaning raw plant materials and agricultural products having a content of valuable ingredients; while these are principally sugar beet and sugar cane, with their important ingredient sucrose, they are also chicory, with its important ingredient inulin, as well as oil seeds for obtaining oil, grapes for obtaining grape juice, or fruits which are used for obtaining vegetable dyes such as carotene or flavoring agents. "Biological material" is furthermore understood as meaning plants or plant constituents which are used for isolating starch.

BRIEF DESCRIPTION OF THE FIGURE

The FIGURE provides a schematic diagram of a preferred embodiment of a device for practicing the method of the invention.

DETAILED DESCRIPTION OF THE INVENTION

In connection with the present invention, extraction is a separation method for dissolving out particular constituents, in particular ingredients, from solid or liquid substance mixtures, in particular biological material, using suitable solvents, with no chemical reactions taking place between the solvent and the dissolved substance, that is the ingredient of the biological material. Preference is given to using water as the extractant when isolating water-soluble ingredients such as sucrose, inulin or starch from biological material, for example when isolating sugar from sugar beet and/or sugar-beet chips. In a variant, it is possible to additionally or exclusively isolate fat-soluble ingredients from the biological material by using solvents which are predominantly nonpolar and/or organic.

In a particularly preferred embodiment, step a) of the method according to the invention, namely the electroporation of the biological material, is carried out in a conductive medium, with the biological material being subjected to a high-voltage field. Preference is given to providing for the high-voltage field to be generated in a manner known per se, for example by way of voltage-conducting electrodes, by means of applying a voltage, in particular a high voltage, across the biological material. While preference is given to using pulse-shaped high-voltage curves, periodic alternating fields and direct-current fields are also envisaged. The field strength is preferably from about 0.5 to 1.5 kV/cm, in particular from 0.7 to 1.3 kV/cm. In a particularly preferred variant, the conductivity of the medium in which the biological material is located is matched with the conductivity of the biological material such that an optimal field-line curve is achieved within the biological material; the conductivity is preferably from approximately 0.2 to 2.5 mS/cm, in particular from 0.4 to 2.1 mS/cm. In a particularly preferred variant, whole crop plants, for example whole sugar beets, are used for the electroporation. It has been found that this thereby reduces the energy required for the electroporation as compared with the electroporation of comminuted biological material. The invention naturally also provides for the biological material to be supplied to the electroporation in comminuted form as well, for example in the form of beet chips in the case of sugar beet.

According to the invention, preference is given to the cell juice being separated off from the biological material, in step b) in the method according to the invention, under slight mechanical loading. The invention provides for the mechanical loading, that is pressurization, of the biological material in step a), in step b), in step c) and in step d) of the method according to the invention always, that is at any time and in any stage of the method, being less than 2 MPa, in particular less than 1 MPa, preferably less than 0.5 MPa. That is that the pressure on the biological material, or the mechanical loading of the biological material is preferably, according to the invention, exclusively always less than 2 MPa during the whole of the method and that, preferably, no other forces and loadings are exerted on the biological material. According to the invention, particular preference is given to the mechanical loading of the biological material being reduced maximally and the compressive load always being less than 1 MPa, preferably less than 0.5 MPa. In particular, no pressure or no mechanical loading is ever exerted on the biological material. The low mechanical loading is a significantly reduced as compared high mechanical loading, known from the prior art, of more than 2 MPa, chiefly of from approximately 10 to approximately 30 MPa, which is tantamount to the biological material being pressed out.

The low mechanical loading, which is preferred in accordance with the invention, is normally achieved by simply tumbling and/or turning the biological material, for example in a screw which is preferably designed as a full screw. Other devices, which are known per se, and which serve such a purpose, can naturally also be used for tumbling and/or turning the biological material. These devices are preferably all types of conveyor screws such as semienclosed screws as well as conveyor belts, vibratory lines or drums.

It has been found, surprisingly, that a high proportion of cell juice, and consequently a high proportion of the ingredients contained in the biological material, can already be isolated when the biological material, in particular beet or beet chips, which has been pretreated by electroporation is subjected to even slight mechanical loading (see above). As is known, thermally or electrically disrupted beet or beet chips are pressed under high mechanical pressure of more than 2 MPa, mainly of from approximately 10 to 30 MPa, in a conventional pretreatment, for example prior to an extraction, resulting in the beet or the beet chips having to be conveyed into the procedural steps following this pressing in a form which is greatly altered mechanically, i.e. mainly in a pulp-like consistency. By contrast, the biological material which is treated in step b) for the purpose of separating off the cell juice remains, as a result of the slight mechanical loading which is preferred in accordance with the invention, unaltered in its form and character and can consequently be supplied in a mechanically unaltered form, in a simplified manner, to the subsequent step c), namely the extraction.

In addition to this, it advantageously follows that, because of the low mechanical loading, the cell juice which is separated off in step b) is essentially clear and not contaminated with the tissue constituents, in particular suspended substances, etc., which inevitably emerge in connection with high mechanical loading, and can therefore be isolated in particularly pure form. In another variant, the cell juice which is separated off in step b) is further clarified by adding flocculating agent.

In accordance with the invention, step b) of the method according to the invention achieves a pretreatment of the biological material prior to the extraction in the following step c). In accordance with the invention, this pretreatment advantageously makes it possible to separate off the cell juice in advance from the biological material in a particularly effective manner. It has been found that the biological material which has been pretreated in accordance with the invention is, particularly because of the low mechanical loading which is preferred in accordance with the invention, mechanically stable and also packed loosely such that the extractant can very readily flow through the packed material in order to enable a particularly effective extraction to take place.

Another advantage of the method according to the invention is that, as a result of a large quantity of cell juice, and the significant proportion of ingredients which are present therein, having been separated off from the biological material in advance, the downstream extraction has to make a significantly lower contribution to isolating the ingredients from the biological material. In particular, when sugar beet or sugar beet chips are used as the biological material, the quantity of sugar which has to be separated off in the downstream extraction is reduced. In the preferred use of beet or beet chips as the biological material, the yield is from approximately 10 to 30% by mass, based on the total mass of the biological material.

Particularly advantageously, the effect according to the invention leads to a perceptible reduction in the necessary quantity of extraneous water which has to be used for extracting the ingredients of the biological material; according to the invention, there is a perceptible reduction in the withdrawal, that is in the ratio of the quantity of extract to the quantity of biological material employed. In this connection, the withdrawal is reduced down to values of less than 100%, in particular down to approximately 90%. Particularly advantageously, the reduction in the withdrawal which is brought about in accordance with the invention results in an increase in the purity of the extract to values of more than 90%, in particular to approximately 91.5% to 92.5%. As a consequence, the quantity of limestone (milk of lime) which is, for example, to be used for the extract purification procedure, which is preferably envisaged, according to the invention, following the extract isolation in step c), can be significantly decreased, in particular down to values from approximately 15% to approximately 30%.

Without being limited to the theory, the demand placed on the subsequent extraction is significantly reduced firstly by the electroporation in step a), because the electroporation has already opened the cells, and, secondly, by the removal of a large quantity of cell juice from the electroporated biological material in step b), which means that the extraction of the biological material can take place at significantly low temperatures. The method which is preferred in accordance with the invention is therefore also distinguished by the fact that the extraction step c) is carried out at a temperature which is significantly reduced as compared with the prior art, that is a temperature of from 10 to 65° C., preferably of from 45 to 60° C., in particular of from 46 to 60° C.

The extraction temperature can, of course, be adapted to the requirements of the biological material and also be significantly lower or higher, as long as an extraction can still be carried out. Because of the reduction in the extraction temperature, the biological material, for example beet chips, is treated more gently than in the case of the conventional method of thermal denaturation. This advantageously results, in accordance with the invention, in an increase in the ability of the biological material, for example the beet chips, to be pressed out by approximately 2% DM (DM=dry matter) percentage points.

The invention also provides for the purified extract, in particular the thin juice I and II, to be subsequently thickened in a multistep evaporation plant to a dry matter content of approximately 70%. The quantity of energy which is required for the subsequent evaporation of the extraneous water from the extract which has been isolated decreased on account of the reduction in the quantity of extraneous water which is achieved in accordance with the invention.

Preference is given, in accordance with the invention, to isolating the sugar from the extract and/or thin juice, which is/are obtained from the extraction of sugar beet which have been treated in accordance with the invention, in a multi-step crystallization plant. The extracted biological material, in particular the extracted beet chips, are subsequently also dewatered mechanically and, for example, mixed with molasses and, preferably after thermal drying, marketed as feedstuff, in particular as feedstuff pellets.

In a preferred version, the extraction in step c) takes place as an alkaline extraction, in particular using alkylating agents such as milk of lime and/or burnt lime. In this connection, "alkaline" is understood as meaning the pH of an aqueous medium of from approx. pH 7 to approx. pH 14 (at 20° C.). In a preferred variant, the alkaline extraction is carried out at from pH 7.5 to pH 11, in particular at approximately pH 10, for example pH 10.2.

It is not possible, in association with an alkaline extraction, to rule out chemical reactions with the biological material in every case; in particular, a quantity of high molecular weight calcium pectate can be formed. In the case of known extraction temperatures of from approximately 70 to 75° C., these undesirable chemical reactions of the alkaline extraction are so vigorous that large quantities of calcium pectate are formed in some cases, with this significantly impairing the filtration of the isolated extract, which has preferably been purified by means of juice purification, such that a method of this nature cannot be realized in practice. By contrast, the alkaline extraction which is preferred in accordance with the invention, and which is carried out at lower temperatures, reduces the formation of these high molecular weight compounds, thereby making it possible to achieve a filtration coefficient of less than 1 mm/g when filtering the purified extract, in particular the thin juice I and/or thin juice II which is/are obtained by juice purification in connection with extracting the sugar beet.

The alkalinity, for example in the form of milk of lime, calcium hydroxide, calcium saccharate or burnt lime, is preferably already introduced to the biological material, preferably sugar beet, sugar cane or chicory, immediately after the electroporation (step a)), in particular in an intermediate bunker prior to the further processing of the biological material in step b). In another variant, the alkalinity is introduced when separating off the cell juice in step b). In another variant, the alkalinity is introduced immediately prior to carrying out the extraction (step c)).

In a preferred embodiment of the invention, the alkalinization of the biological material, that is preferably of the beet or beet chips, of the sugar cane or of the chicory, is effected by adding the alkalinizing agent directly to the cutting machine. This has the advantage of partially disinfecting the biological material.

In a preferred embodiment of the invention, the alkalinization of the biological material is effected by adding the alkalinizing agent to the bunker of the biological material, in particular the beet bunker, or to the transport path to the bunker, in particular the beet bunker. This has the advantage of achieving partial disinfection.

Preference is given, in accordance with the invention, to normally introducing the alkalinity to the biological material in the form of aqueous solutions, which are preferably sprayed on. In another variant, at least one alkaline substance, in particular lime such as burnt lime, is introduced into the procedure as a solid, preferably in powder form, for the purpose of introducing the alkalinity to the biological material.

As a result of the alkalinity being introduced to the biological material at, in particular, an early phase of the method according to the invention, preferably in step b) or immediately prior to this step, the separated-off cell juice is already particularly advantageously, according to the invention, subjected to a purification directly during the process of being separated off from the biological material. In the preferred use involving beet or beet chips, non-sugar substances, mainly proteins, are eliminated in advance in this way. In this connection, a large part of the non-sugar substances remains adsorbed to, or coagulated on, the beet chips even until after the extraction. A supplementary purification of the separated-off cell juice can naturally also be carried out subsequently in a manner known per se.

In addition, introducing the alkalinity to the biological material reduces the risk of the biological material becoming infected and increases the microbiological stability of the biological material and of the separated-off cell juice during the processing. In this connection, the microbiological stability is approximately $10^4$ CFU/ml.

In another preferred variant, at least one auxiliary substance is supplied to the biological material in the method according to the invention, preferably in step b). In connection with the present invention, an "auxiliary substance" is understood as being a composition or pure chemical substance which has no function whatsoever in the isolated ingredient, preferably in the isolated foodstuff. These auxiliary substances are process substances such as condensate and also process water, solvents, disinfectants such as formaldehyde, or antifoaming agents. They are preferably also flocculation aids such as cationic or anionic flocculation aids, or substances for introducing alkalinity and/or calcium ions, such as milk of lime, burnt lime, calcium hydroxide, calcium saccharate, calcium sulfate and other calcium salts and/or aluminum salts. The at least one auxiliary substance which is preferably supplied in accordance with the invention is normally introduced into the biological material in the form of a solution, which is preferably sprayed on. In another variant, the at least one auxiliary substance is introduced as a solid, preferably in powder form. The auxiliary substances which are introduced also bring about a preliminary purification of the separated-off cell juice.

Particularly advantageously, the electroporation, in accordance with the invention, of the biological material in step a) opens its cell walls such that the introduction of alkalinity and/or calcium ions into the biological material is particularly facilitated in step b) during the removal of the cell juice from the biological material. In particular, the combination, which is preferred in accordance with the invention, of electroporation in step a) and the alkaline extraction in step c) results in a further increase in the ability of the biological material to be dewatered, for example by being pressed out, by up to approximately 8% points of dry matter content (% DM), after the method according to the invention has been completed.

The present invention therefore preferably also relates to a method for increasing the ability of extracted biological material, in particular sugar beet chips, to be pressed out and consequently for increasing the dry matter content which can be achieved in connection with the pressing-out, characterized in that an electroporation of the biological material, in particular of sugar beet, is carried out in a first step and an alkaline extraction of the electroporated biological material, in particular electroporated sugar beet or sugar beet chips, sugar cane or chicory, is carried out in a further step and extracted biological material having an increased of the ability to be pressed out is subsequently obtained.

The present invention therefore also preferably relates to a method for obtaining extracted biological material, in particular extracted sugar beet chips, sugar cane or chicory, having a high dry matter content, preferably of approximately 38% DM, characterized in that the biological material, in particular sugar beet, is electroporated in a first step, the electroporated biological material, in particular electroporated sugar beet or sugar beet chips, is subjected to alkaline extraction in a further step, the electroporated biological material, in particular electroporated sugar beet or sugar beet chips, is pressed out, preferably in a manner known per se, in a subsequent step and extracted biological material having an elevated dry matter content is then obtained.

In another preferred variant, the biological material is additionally comminuted, for example in the case of the sugar beet being converted into beet chips, in a further procedural step between procedural steps a) and b). This is done in order to still further facilitate the removal of cell juice from the electroporated biological material.

In a preferred variant of this method, the procedural step b) additionally already takes place within a delivery shaft or buffer shaft which is arranged at the section of the screw which is designed for receiving the biological material. The mechanical preliminary pressure which is exerted on the biological material both in the delivery shaft and in the full screw is preferably always less than 2 MPa, particularly preferably less than 1 MPa, preferably less than 0.5 MPa. Particularly preferably, no preliminary pressure is exerted. The delivery shaft which is preferably provided naturally serves to temporarily store and accumulate the biological material for uptake into the screw; the pressure which is exerted on the biological material in this connection is regarded as being negligible. In particular, it is just high enough for the biological material which has been accumulated in the delivery shaft to be delivered, in a manner known per se, into the screw with a high degree of efficiency and for the screw to exhibit a satisfactory degree of filling.

In one variant, the outer jacket and/or the screw threads, i.e. the screw, of the screw which is preferably employed in accordance with the invention is/are perforated. That is, they exhibit holes through which the cell juice which has separated off from the biological material can escape from the screw. Particular preference is given to the outer jacket and the screw threads being perforated. The cell juice which is released, in particular while the biological material is being transported through the screw, that is the conveyor juice, penetrates through the perforated screw threads and/or the perforated outer jacket of the screw and collects in a tank which is normally arranged, in accordance with the invention, at the screw and, in particular, surrounds the screw. This tank normally opens out into an outlet line, preferably at the lowest point.

In another variant, the delivery shaft, that is the buffer shaft, in which the electroporated material collects before delivery into the section of the screw which is designed for receiving the biological material, is provided with an outflow, preferably at the lowest point of the buffer shaft. A substantial proportion of the cell juice which has been separated off from the biological material in the buffer shaft escapes by way of the outflow which is preferably provided.

The present invention therefore also relates to a device for isolating ingredients from biological material, which device is normally employed for implementing the method according to the invention. According to the invention, this device exhibits an appliance, in particular a chamber, for electroporating the biological material as well as at least one full screw for receiving the electroporated biological material, for the purpose of separating off cell juice from the biological material, and an extractor for extracting the biological material. According to the invention, the at least one full screw is perforated at its outer jacket and/or its screw threads. A tank for receiving the cell juice which has separated off in the full screw, which tank preferably surrounds the full screw and, in particular, seals it off hermetically, is preferably arranged at the full screw. The function of the at least one full screw according to the invention essentially comprises tumbling the biological material, that is slightly loading it mechanically. This is preferably combined with the preferred further function of the full screw, namely conveyance of the biological material through the device, preferably from the electroporation device to the extractor.

Preference is given, according to the invention, to the extractor being a mixer-settler tower. In one variant, the extractor is a trough screw extractor such as a DDS extractor. In another variant, the extractor is a drum cell extractor such as an RT drum.

In another preferred embodiment, the device according to the invention contains a slicer/shredder, that is a cutting machine, preferably a drum cutting machine, which is arranged in the path of conveyance of the biological material from the electroporation device to the full screw and which further comminutes the electroporated biological material prior to delivery of the latter to the full screw. In one variant, the slicer/shredder is provided with an intermediate bunker for receiving the electroporated biological material prior to the comminution, with this primarily providing, by means of the stacking of the biological material, the necessary advance pressure for comminuting it.

A mash container is preferably also assigned to the section of the screw which is designed for releasing the transported biological material, in which mash container the biological material emerging from the screw is collected, preferably for the purpose of the subsequent extraction of the biological material in the extractor.

In a preferred embodiment of the device according to the invention, at least one metering device is additionally provided for introducing auxiliary substances and/or alkalinity. In one variant, this metering device contains at least one washing line having at least one nozzle head, which is connected to it, for spraying solutions of auxiliary substances and/or alkalinizing agents such as milk of lime onto the biological material, which is preferably located in the full screw. In another variant, the at least one metering device is a device which serves for introducing solids, preferably pulverulent media; in particular, this device is a pneumatic feeder and/or a spiral conveyor.

The metering device is preferably arranged in a metering region of the full screw, in particular above its outer jacket. In one variant, the metering device is arranged in a metering region of the intermediate bunker. In another variant, the metering device is arranged in a metering region of the mash container. In this connection, a "metering region" is understood as being that circumscribed space from which the metered substances, that is the above-mentioned auxiliary substances, alkalinizing agents, etc., can be introduced into or onto the biological material by way of the chosen metering device.

In another preferred variant, the section of the screw which is designed for receiving the electroporated biological material is preferably located at a lower point at the beginning of the screw, whereas the section of the screw which is designed for releasing the transported biological material is preferably located at an upper point at the end of the screw, with this upper point being situated above the aforementioned lower point. That is, the full screw which is provided in accordance with the invention is arranged along a gradient, with the biological material being transported in the full screw from the lower point to the upper point against the gradient.

Other advantageous embodiments ensue from the subclaims.

The device according to the invention is explained in more detail by the FIGURE: the FIGURE shows a diagram of a preferred embodiment of the device according to the invention, which device exhibits an appliance for the electroporation of the biological material (1), a cutter (3) for comminuting the electroporated biological material having an intermediate bunker (2) and a delivery shaft (4), a perforated full screw (5) having a receiving tank, at least one metering device (6) for introducing auxiliary substances to the biological material, an outflow (7) for collecting juices from the delivery shaft and from the full screw, and an extractor (8).

EXAMPLES

The invention is clarified with the aid of the following examples:

Example 1

Alkaline Extraction of Electroporated Beet Material

Directly harvested or stored sugar beets are washed and then impinged, in coarsely shredded form or uncut, with high voltage pulses of from 0.7 to 1.5 kV/cm in an electroporation unit (1). During this time, the beets or beet chips are present in a conductive medium having a conductivity of from 0.4 to 2.1 mS/cm. The electroporation opens up the cell walls in a known manner.

The electroporated beets or beet chips are then conveyed into an intermediate bunker (2) directly above the cutting machine (3), passed from there into the cutter (3), are comminuted and then passed, by way of a delivery shaft (4), into a full screw (5), whose outer jacket and screw threads are perforated in order to enable the cell juice, that is the conveyor juice, which emerges from the beet chips to escape. Milk of lime is metered into the intermediate bunker for the purpose of reducing microbiological activity.

The closed full screw has the task of transporting the electroporated chips to the chip mash in the mash container of the extractor (8) which is provided therefor. The disposition of the full screw exhibits a gradient which leads upward in the direction of transport. That is, the lowest point of the full screw is situated directly below the delivery site (4) between the cutting machine (3) and the screw (5). Its highest point is situated directly in front of the drop shaft of the chip mash. A delivery shaft (4), which is designed as a buffer shaft, is located between the exit from the cutting machine and the entry to this full screw, which is designed as a conveyor screw. The fresh electroporated beet chips collect in the delivery shaft (4). An outflow (7) is located at the lowest point of the screw. This outflow is used for collecting cell juices which emerge from the electroporated chips during conveyance in the screw and/or during the mechanical pressurization in the delivery shaft.

While the screw (5) has, in the first place, the task of transporting the electroporated chips to the chip mash, it also has, in the second place, the task of impinging mechanically on, or tumbling, the chip material during conveyance of the latter against the gradient. In this connection, the mechanical preliminary pressure from the delivery shaft is always less than 2 MPa. This maximum pressure value applies for the whole installation, that is, on the path from the cutting machine to the chip mash through the described installation, the electroporated chip material is subject to a pressure which is at any time less than 2 MPa.

The conveyor juice which is released during conveyance of the chips through the screw (5) penetrates through the perforated outer jacket of the screw and collects in a tank which surrounds the full screw and opens out into the above-described outlet (7) at the lowest point of the screw. During the conveyance of the electroporated chips in the full screw, cell juices from the electroporated chips escape through the perforation of the full screw and the perforation of the outer wall of the screw and are collected, and conducted to the outflow (7), in the tank which is arranged under the full screw. In this connection, the tank encloses the full screw hermetically.

Washing lines are arranged, in the axial direction of the screw, between the tank and the outer jacket of the screw. The washing lines possess nozzle heads which serve as the metering device (6) by way of which auxiliary substances are sprayed from the outside onto the outer jacket of the full screw. In a modification, several metering sites having nozzles in the interior of the full screw are arranged directly from the beginning of the full screw and in the direction of conveyance in the full screw up to about the point in the full screw at which, when the screw is operating normally, the chips still have a further dwell time of approximately 5 minutes in the screw. Auxiliary substances are metered into the conveyed chip pack by way of these nozzles. A calcium saccharate solution is added to the chips, on their route to the chip mash, by way of the auxiliary substance addition sites in the intermediate bunker and in the full screw. As an alternative, milk of lime or dry lime is added to the chips. The chips absorb the major part of this solution. In this connection, the chips take up calcium and are in this way prepared for an alkaline extraction, which is carried out in a manner known per se. The quantities of calcium saccharate or lime or milk of lime which are not taken up by the chips collect at the lowest point of the screw and are conducted away from there, together with the cell juice, that is the conveyor juice, and subjected to further processing.

The beet chips which have been tumbled in front of the screw are supplied, by way of the mash container, to a countercurrent extraction unit and extracted in this unit; the extract is then collected. The temperature of the extraction is from 45 to 60° C.; preference is given to selecting a temperature which is significantly above 45° C. but which is at most 60° C. The extractor is a mixer-settler tower, a trough screw extractor or a drum cell extractor. In the extractor, the chips are extracted in countercurrent to the extracting agent (what is termed fresh water).

Following on from this, a milk of lime-carbonic acid juice purification is carried out. The purified extract (thin juice I and II) is processed further in a conventional manner; that is, after the juice has been thickened to give a syrup, the sugar is isolated in crystallizers by means of further evaporation and successive crystallization. The calcium carbonate sludge which has been separated off is dewatered conventionally using filter presses and marketed as a fertilizer, i.e. what is termed Carbokalk.

After prior alkalinization, a flocculation aid is metered into the cell juice which has been separated in the full screw and/or in the delivery shaft. The conveyor juice is then fed to a conventional static decanter. The fines in the decanter are drawn off and supplied to the preliming unit of the extract work-up which is being carried out in parallel. The clear runoff in the decanter is, on the other hand, fed through to its further use, which comprises combining it with thin juice from the extract work-up. In parallel with this, the accruing extract is subjected to a conventional juice purification.

The extracted chips are pressed out in screw presses. The pressed-out press water is returned to the extractor. The pressed chips are thermally dewatered conventionally, that is in low temperature dryers, high temperature dryers or evaporation dryers.

Example 2

Pilot Plant-Scale Method

Pilot plant-scale experiments (processed beets: 6 kg/h) are presented below in order to illustrate the advantageous nature of the method.

Procedural Step of Cutting and Alkalinizing the Beet

Beets were electroporated in an electroporation apparatus at a field strength of from 0.7 to 1.5 kV/cm and then shredded in a pilot-plant slicer/shredder (Alexander-werk). The chips were then transferred to a mixer and treated with milk of lime (slaked lime solution). In this connection, care was taken to ensure that the chip temperature was less than 20° C. The quantity of slaked lime solution (concentration: 220 g of CaO/l) corresponds to an addition of effective alkalinity of from 0.3 to 0.5 g of CaO/100 g of beet. The alkalinized beets were transferred to a trough screw of the DDS type. The outer jacket and the screw threads of the conveyor screw are perforated. The chip mass was conveyed through the conveyor screw while being tumbled gently. On the way, from approx. 20 to 30% of alkalinized sugar beet juice was separated off, based on the beet mass employed. The alkaline sugar beet juice (pH: from 11 to 12) was collected.

Procedural Step of Extraction

The alkaline chips were transferred to a trough screw extractor of the DDS type and extracted in it. Chips and extraction water (water which is weakly alkalinized and hardened with milk of lime (pH=9.5; 80° dH)) were conveyed in countercurrent to the chip material. In a semicontinuous operation, previously de-juiced chips were extracted at an order of size of 4.8 kg per hour in conjunction with an addition of fresh water of from 60 to 80% based on the chip mass. The extraction was carried out at a temperature of 60° C., which is reduced as compared with the conventional method.

This results, particularly advantageously, in the method consuming less energy and in the chip material being treated more gently. This manifests itself, in particular, in superior extract quality (higher purity) and superior pressability in connection with the downstream pressing-out of the chips.

In the experiments, the main advantage of the alkaline extraction in combination with the electroporation was found to be a greater ability to press out the extracted chips (pressing-out in a ram press) than in the case of the conventional method, with this leading to the pressed chips having a dry matter content which was markedly higher, i.e. by approx. 8% points. For example, the dry matter content is increased to 38% DM as compared with 30% DM in the case of conventional methods. This results in a significantly lower consumption of energy in the subsequent thermal dewatering of the chips.

The extract purity is in the range of from 91.5 to 92.5% and consequently significantly higher than in the case of the conventional method. Important non-sugar substances, such as proteinaceous substances and pectins, which are extracted in the case of the conventional method remain in the chips in association with the alkaline treatment and increase their feedstuff value in connection with the downstream processing to give feedstuff pellets.

When the method is carried out industrially, the press water which is obtained in connection with pressing out the extracted chips is returned to the extraction unit. In this connection, the high purity of the press water, which is about 89%, has an advantageous effect.

Procedural Step of Juice Purification

The alkaline conveyor juice and the alkaline extract were combined. The juice purification was carried out in a laboratory juice-purifying apparatus (three-necked flask with temperature control option). The mixture was treated with milk of lime (concentration 220 g of CaO/l) (up to an alkalinity of from 0.4 to 0.6 g of CaO/100 ml of extract). An alkaline treatment of the juice was then carried out at 85° C. This procedural step serves to break down invert sugar and acid amides, which would interfere with the subsequent process. The subsequent procedural steps largely correspond to those of the conventional method. In the first and second carbonations, calcium carbonate is precipitated out by passing in carbon dioxide, with the calcium carbonate adsorptively binding the non-sugar substances which are present in the juice and removing them from the juice as a result of the subsequent filtration. At the end of the juice purification, a purified extract is obtained.

The experiments showed that the purified extract is of high quality, that is has less color (from approx. 600 to 800 I.U.) as compared with the conventional method (greater than 1000 I.U.). The stability of the purified extract toward thermal stress in connection with the subsequent inspissation of the juice is also high. In a laboratory test (boiling for one hour while refluxing the condensate) a slight discoloration of the juice of only approx. 25 I.U. occurred. A disadvantage of the method is the relatively high content of soluble calcium ions, what are termed the lime salts.

It is possible to dispense with the procedural step of preliming, which provides for a progressive pre-alkalinization under mild conditions of temperature and alkalinity.

The calcium carbonate precipitates which were separated off contained fewer non-sugar substances than in the case of the conventional method. This increases the fertilizer value of the Carbokalk.

Summary of the Results:

The pretreatment of the beet by means of the mechanical pressurization in the full screw and in the delivery shaft separates off a substantial proportion of the cell juice from the beet material. The yield in this connection is from approximately 10 to 30% cell juice based on the mass of the introduced beet material.

The prior removal of the cell juice reduces the quantity of sugar which has to be separated off in the subsequent extraction, with this resulting in a perceptible reduction in the withdrawal down to approximately 90%.

Reducing the withdrawal results in the purity of the extract being increased to approximately 92%.

The electroporated chip material is extracted in the countercurrent extraction at a low temperature, that is at a temperature of from 45 to 60° C., preferably of always more than 45° C. and always less than 60° C. The mild treatment of the chip material in connection with the extraction gives rise to further advantages for the quality (purity) of the extract.

The ability of the chips to be pressed out after the alkaline extraction is increased. The gain in dry matter amounts to 8% points, for example from 30% DM to 38% DM.

The decrease in the quantity of fresh water which is required reduces the water evaporation which is necessary.

The prior removal of the conveyor juice increases the separate treatment in a downstream juice purification unit. Because of its higher purity, the possibility of a prior removal of the non-sugar substances which are dissolved in the conveyor juice presents itself.

The mixture composed of highly pure conveyor juice and extract from the subsequent extraction leads to purer juices than can be obtained in conventional methods.

The alkalinization of the beet chips and of the cell juice which is separated off from the chips increases their microbiological stability to a value of $10^4$ CFU/ml.

What is claimed is:

1. A method for isolating ingredients from biological material, comprising the steps of:

a) electroporating biological material, b) separating off cell juice from the electroporated biological material under a sufficiently low mechanical loading such that the biological material remains substantially unaltered in its form and character and is consequently supplied to a subsequent alkaline extraction treatment in such substantially mechanically unaltered form, c) subjecting the electroporated biological material from which the cell juice has been separated off in step b) above to an alkaline extraction treatment in which ingredients of said biological material are dissolved out of said material by contacting the material with at least one suitable solvent at a pH of from about 7 to about 14 to produce an extract, d) obtaining the ingredients of the biological cell material in the cell juice and in the extract.

2. The method as claimed in claim 1, wherein the biological material in step a) is subjected to a high voltage field in a conductive medium.

3. The method as claimed in claim 1, wherein mechanical pressurization of the biological material is always less than 0.5 MPa.

4. The method as claimed in claim 1, wherein step b) takes place in a screw.

5. The method as claimed in claim 1, wherein, in step b), the biological material is supplied with at least one auxiliary substance.

6. The method as claimed in claim 1, wherein step c) is carried out at a temperature of from 0 to 65° C.

7. The method as claimed in claim 1, wherein the biological material comprises at least one of sugar beet (Beta vulgaris) and sugar beet chips.

8. The method as claimed in claim 1, wherein the biological material comprises chicory.

9. A device for isolating ingredients from biological material according to the method as claimed in claim 1, said device comprising at least one appliance for electroporation (1) and at least one extractor (8), wherein at least one full screw (5) for receiving the electroporated biological material is arranged between the appliance for the electroporation (1) and the extractor (8), said full screw (5) configured to separate off the cell juice from the electroporated material under a sufficiently low mechanical loading such that the biological material remains substantially unaltered in its form and character and is consequently supplied to the alkaline extraction treatment step in such substantially mechanically unaltered form.

10. The device as claimed in claim 9, wherein the at least one full screw (5) is designed as a conveyor screw and wherein a first section of the screw which is designed for receiving the electroporated biological material is formed at a lower point, and a second section of the screw which is designed for releasing the conveyed biological material is formed at an upper point, of a gradient which exists between said first and said second sections.

11. The device as claimed in claim 9, further comprising at least one metering device (6) for metering auxiliary substances.

12. The method as claimed in claim 1, wherein said mechanical loading comprises tumbling.

13. The method as claimed in claim 4, wherein said screw is a full screw.

14. The method as claimed in claim 5, wherein the auxiliary substance is at least one of lime and milk of lime.

15. The method as claimed in claim 6, wherein step c) is carried out at a temperature of from 45 to 60° C.

16. The device as claimed in claim 9, wherein the full screw is threaded and at least one of an outer jacket of said screw and said screw threads is perforated.

17. A method for isolating ingredients from a biological material selected from the group consisting of chicory and sugar cane, said method comprising the steps of:

a) electroporating the biological material;

b) separating off cell juice from the electroporated biological material under a sufficiently low mechanical loading such that the biological material remains substantially unaltered in its form and character and is consequently supplied to a subsequent solvent extraction treatment in such substantially mechanically unaltered form;

c) extracting the biological material from which the cell juice has been separated off in step b) above by dissolving ingredients out of the material upon contacting the material with at least one suitable solvent; and d) obtaining the ingredients of the biological cell material in the cell juice and in the extract.

18. The method as claimed in claim 17, wherein the biological material in step a) is subjected to a high voltage field in a conductive medium.

19. The method as claimed in claim 17, wherein said mechanical loading comprises tumbling.

20. The method as claimed in claim 17, wherein mechanical pressurization of the biological material is always less than 0.5 MPa.

21. The method as claimed in claim 17, wherein step b) takes place in a screw.

22. The method as claimed in claim 21, wherein said screw is a full screw.

23. The method as claimed in claim 17, wherein, in step b), the biological material is supplied with at least one auxiliary substance.

24. The method as claimed in claim 23, wherein the auxiliary substance is at least one of lime and milk of lime.

25. The method as claimed in claim 17, wherein step c) is carried out at a temperature of from 0 to 65° C.

26. The method as claimed in claim 25, wherein step c) is carried out at a temperature of from 45 to 60° C.

* * * * *